United States Patent

Iwasaki et al.

[11] Patent Number: 6,069,216
[45] Date of Patent: May 30, 2000

[54] CATIONIC GROUP-CONTAINING COPOLYMER AND THICKENER

[75] Inventors: Masaki Iwasaki; Tadanori Yoshimura, both of Wakayama; Takashi Matsuo, Tokyo; Koji Yui, Wakayama, all of Japan

[73] Assignee: Kao Corporation, Tokyo, Japan

[21] Appl. No.: 09/089,358

[22] Filed: Jun. 3, 1998

[30] Foreign Application Priority Data

Jun. 11, 1997 [JP] Japan .................... 9-153436
Oct. 17, 1997 [JP] Japan .................... 9-285176

[51] Int. Cl.$^7$ .................... C08F 126/06
[52] U.S. Cl. .............. 526/258; 526/265; 526/304; 526/305; 526/307.2; 526/307.7
[58] Field of Search .................... 526/258, 265, 526/304, 305, 307.2, 307.7

[56] References Cited

U.S. PATENT DOCUMENTS

| | | |
|---|---|---|
| 5,100,660 | 3/1992 | Hawe et al. . |
| 5,362,827 | 11/1994 | Bock et al. ............. 526/307.2 |
| 5,698,627 | 12/1997 | Oguni et al. ............. 526/307 |
| 5,700,892 | 12/1997 | Takiguchi et al. ............. 526/306 |

FOREIGN PATENT DOCUMENTS

| | | |
|---|---|---|
| 0 419 654 | 4/1991 | European Pat. Off. . |
| 37 30 781 | 3/1989 | Germany . |
| 51-46586 | 4/1976 | Japan . |
| 4-20584 | 1/1992 | Japan . |
| 4-183772 | 6/1992 | Japan . |
| 5-140531 | 6/1993 | Japan . |

*Primary Examiner*—Bernard Lipman
*Attorney, Agent, or Firm*—Oblon, Spivak, McClelland, Maier & Neustadt, P.C.

[57] ABSTRACT

A cationic group-containing copolymer is provided which possesses excellent thixotropy and exhibits high adsorbability to the skin, hair, etc. and, when incorporated as a thickener in cosmetic articles, manifests a very satisfactory tactile sensation. The cationic group-containing copolymer is characterized in that the viscosity at 25° C. of the aqueous solution prepared by incorporating the copolymer in deionized water at a concentration of 0.5 wt. % is in the range of 0.3–20 Pa·sec. at a shear rate of 1 sec$^{-1}$ and in the range of 0.01–5 Pa·sec. at a shear rate of 10 sec$^{-1}$ and the viscosity at a shear rate of 1 sec$^{-1}$ is higher than the viscosity at a shear rate of 10 sec$^{-1}$. This cationic group-containing copolymer is obtained by particularly using a cationic group-containing vinyl monomer, a hydrophilic nonionic group-containing vinyl monomer such as N,N-dimethyl (meth)acrylamide or N,N-diethyl (meth)acrylamide, and a cross-linking vinyl monomer containing at least two vinyl groups in the molecular unit thereof as essential component monomers and radically polymerizing the essential component monomers. A thickener made of the copolymer is also disclosed.

9 Claims, 1 Drawing Sheet

CATIONIC GROUP-CONTAINING COPOLYMER AND THICKENER

FIELD OF THE INVENTION

The present invention relates to a cationic group-containing copolymer and a thickener which is made thereof. More particularly, the present invention relates to a cationic group-containing copolymer which is advantageously usable as an additive for chemical products and cosmetic articles and particularly as a thickener producing a fine tactile sensation and a thickener which is made of this copolymer.

DESCRIPTION OF PRIOR ARTS

At present, various kinds of thickener are utilized in various industrial fields. As these thickeners, natural high polymers such as, for example, carboxymethyl cellulose, methyl cellulose, hydroxyethyl cellulose, starch, xanthan gum and sodium alginate have been known. These thickeners generally are deficient in thixotropy and, when used as an additive for cosmetic articles, do not exhibit a very good coating property.

JP-A-51-46586, for example, discloses the alkali metal salt of a cross-linked polymer of polyacrylic acid. This alkali metal salt, though possessing thixotropy and exhibiting a tolerable coating property, is not highly satisfactory in terms of tactile sensation, particularly so prominently when it is applied to the hair.

JP-A-04-20584 proposes a compound produced by copolymerizing a cationic vinyl monomer and a N-vinyl type nonionic monomer in the presence of a cross-linking agent. With the cross-linking agent disclosed in the specification of this patent publication, however, the cross-linking agent manifests no satisfactory polymerizability to the N-vinyl type nonionic monomer such that the points of cross-linkage are not easily introduced uniformly into the molecular chains of polymer throughout the entire course of polymerization from the initial stage to completion. Since the cross-linking agent is not effectively used and the compound is not sufficiently cross-linked, therefore, the produced compound, when added to water, tends to transform into a highly heterogeneous gel.

JP-A-05-140531 and JP-A-04-183772 propose such compounds as are obtained by polymerizing an amine-containing (meth)acryl type monomer or other vinyl monomer in the presence of a cross-linking agent and neutralizing the resultant polymers. In this case, since the amino group in the polymer is neutralized into a cation as with an acid compound, the thixotropy of the hydrogel tends to be largely varied as by the pH in the system. When the compounds mentioned above are used as an additive for cosmetic articles, they are found to produce no high tactile sensation such as an easy spreading on the skin and an intense sensation of residuality of hydrogel.

DISCLOSURE OF THE INVENTION

The task to be fulfilled by the present invention, therefore, is to provide a copolymer which possesses an excellent thixotropy and exhibit a high adsorbability to the skin, hair, etc. When incorporated in cosmetic articles, the copolymer manifests an unusually satisfactory tactile sensation, such as an easy spreading on the skin and a fine tactile sensation of the residue of hydrogel. Then a thickener is made of the copolymer.

The present inventors, after a diligent study pursued with a view to fulfilling the object mentioned above, have discovered that a cationic group-containing copolymer possessing a specific thixotropy exhibits a high adsorbability to the skin, hair, etc. and, when incorporated as a thickener in cosmetic articles, manifests a very satisfactory tactile sensation such as an easy spreading on the skin and a fine tactile sensation of the residue of hydrogel. The present invention has been perfected as a result.

The thickener may be a rheology controller.

The present invention is directed to providing a cationic group-containing copolymer characterized in that the viscosity at 25° C. of the solution prepared by incorporating the copolymer in deionized water at a concentration of 0.5 wt. % is in the range of 0.3–20 Pa·sec. at a shear rate of 1 sec$^{-1}$ and in the range of 0.01–5 Pa·sec. at a shear rate of 10 sec$^{-1}$ and the viscosity at a shear rate of 1 sec$^{-1}$ is higher than the viscosity at a shear rate of 10 sec$^{-1}$ and a thickener made of the copolymer.

The present invention is further directed to a cationic group-containing copolymer obtained by radically polymerizing at least one cationic group-containing vinyl monomer, at least one hydrophilic nonionic group-containing vinyl monomer represented by the formula (I) or (II) and at least one cross-linking vinyl monomer containing at least two vinyl groups in the molecular unit thereof as essential component monomers.

The invention provides a thickener made of the copolymer.

The formulae are:

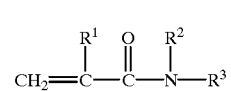

(I)

wherein $R^1$ represents a hydrogen atom or methyl group and $R^2$ and $R^3$ are identical to or different from each other and each represent a hydrogen atom or a linear or branched alkyl group or alkenyl group of one to four carbon atoms;

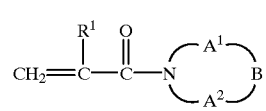

(II)

wherein $R^1$ has the meaning mentioned above, $A^1$ and $A^2$ are identical to or different from each other and each represent a group represented by the formula, —$(CH_2)_n$— in which n represents an integer of 2–6, and B represents —O— or —$CH_2$— group.

DETAILED DESCRIPTION OF THE INVENTION

Now, the mode of embodying the present invention will be described in detail below.

[Cationic group-containing copolymer]

The cationic group-containing copolymer of the present invention is required, for the purpose of manifesting a satisfactory tactile sensation aimed at by the invention, to exhibit such thixotropy that the viscosity at 25° C. of the aqueous solution prepared by incorporating the copolymer in deionized water at a concentration of 0.5 wt. % is in the range of 0.3–20 Pa·sec. at a shear rate of 1 sec$^{-1}$ and in the range of 0.01–5 Pa·sec. at a shear rate of 10 sec$^{-1}$ and the viscosity at a shear rate of 1 sec$^{-1}$ is higher than the viscosity at a shear rate of 10 sec$^{-1}$. This copolymer, when the behavior of viscosity thereof deviates from the range mentioned above, is incapable of producing a fine tactile sensation because it no longer allows easy application to the skin or imparts the sensation of residuality to the skin.

The preferred behavior of viscosity to be exhibited by the cationic group-containing copolymer of the present invention is such that the viscosity at 25° C. of the aqueous solution prepared by incorporating the copolymer in deionized water at a concentration of 0.5 wt. % is in the range of 0.4–10 Pa·sec. at a shear rate of 1 sec$^{-1}$ and in the range of 0.05–3 Pa·sec. at a shear rate of 10 sec$^{-1}$ and the viscosity at a shear rate of 1 sec$^{-1}$ is higher than the viscosity at a shear rate of 10 sec$^{-1}$.

Further, the cationic group-containing copolymer of the present invention manifests a very satisfactory tactile sensation when the aqueous solution prepared by incorporating the copolymer in deionized water at a concentration of 0.5 wt. % exhibits at 25° C. such physical constants originating in dynamic viscoelasticity as a complex modulus of elasticity of not less than 1 N/m$^2$ and not more than 300 N/m$^2$ and a loss tangent (tan δ) of not more than 2, preferably not more than 1.5, and more preferably not more than 1, when the frequency is 6.28 rads/sec and the strain is 1%, and preferably a complex modulus of elasticity of not less than 0.01 N/m$^2$ and not more than 30 N/m$^2$ and a loss tangent (tan δ) of not less than 1 when the frequency is 6.28 rads/sec and the strain is 500%.

The cationic group-containing copolymer of the present invention is capable of conferring thickened on (imparting thixotropy to) such hydrophilic solvents as ethanol and isopropyl alcohol. In order that the fine tactile sensation aimed at by the present invention may be manifested in such an organo gel, it is preferred that the viscosity at 25° C. of the solution prepared by incorporating the copolymer in ethanol at a concentration of 2.0 wt. % is in the range of 0.3–20 Pa·sec. at a shear rate of 1 sec$^{-1}$ and in the range of 0.01–5 Pa·sec. at a shear rate of 10 sec$^{-1}$ and the viscosity at a shear rate of 1 sec$^{-1}$ is higher than the viscosity at a shear rate of 10 sec$^{-1}$.

The cationic group-containing polymer of the present invention which is possessed of the quality described above is highly useful as a thickener in such hydrophilic mediums as aqueous mediums or lower alcohols of 1–3 carbon atoms (ethanol, isopropyl alcohol, etc.), in or mixed mediums thereof.

As the cationic group-containing copolymer exhibiting the thixotropy mentioned above, for example, such cationic group-containing copolymers as are obtained by using at least one cationic group-containing vinyl monomer, at least one hydrophilic nonionic group-containing vinyl monomer represented by the general formula (I) or (II) mentioned above, and at least one cross-linking vinyl monomer containing at least two vinyl groups in the molecular unit thereof as essential component monomers and radically polymerizing the essential component monomers may be cited. These cationic group-containing copolymers will be described below.

[Cationic group-containing vinyl monomer]

As concrete examples of the cationic group-containing vinyl monomer, i.e. one of the component monomers of the cationic group-containing copolymer of the present invention, acid-neutralized compounds or quaternary ammonium salts of amino group-containing monomers including dialkylamino group-containing (meth)acrylic esters or (meth)acrylamides such as dimethylaminoethyl (meth)acrylate, diethylaminoethyl (meth)acrylate, dipropylaminoethyl (meth)acrylate, diisopropylaminoethyl (meth)acrylate, dibutylaminoethyl (meth)acrylate, diisobutylaminoethyl (meth)acrylate, di-t-butylaminoethyl (meth)acrylate, dimethylaminopropyl (meth)acrylamide, diethylaminopropyl (meth)acrylamide, dipropylaminopropyl (meth)acrylamide, diisopropylaminopropyl (meth)acrylamide, dibutylaminopropyl (meth)acrylamide, diisobutylaminopropyl (meth)acrylamide, and di-t-butylaminopropyl (meth)acrylamide, dialkylamino group-containing styrenes such as dimethylamino styrene and dimethylaminomethyl styrene, vinyl pyridines such as 4-vinyl pyridine and 2-vinyl pyridine, N-vinyl heterocyclic compounds such as N-vinyl imidazole, and vinyl ethers such as aminoethyl vinyl ether and dimethylaminoethyl vinyl ether; and diallyl-having quaternary ammonium salts as dimethyldiallyl ammonium chloride and diethyl diallyl ammonium chloride may be cited.

Of these cationic group-containing vinyl monomers, that which proves to be particularly advantageous is at least one member selected from among the compounds represented by the following formula (III) or (IV):

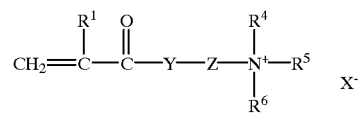

(III)

wherein R$^1$ has the meaning mentioned above, R$^4$ and R$^5$ are identical to or different from each other and each represent an alkyl group or alkenyl group of one to four carbon atoms, R$^6$ represents a hydrogen atom or an alkyl group of one to four carbon atoms, Y represents a —O—, —NH—, or —O—CH$_2$CH(OH)— group, Z represents a linear or branched alkylene group of one to four carbon atoms and X represents a conjugate base of the acid, a halogen atom, or an alkyl sulfate group of one to four carbon atoms,

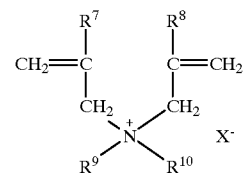

(IV)

wherein R$^7$ and R$^8$ are identical to or different from each other and each represent a hydrogen atom or a methyl group, R$^9$ and R$^{10}$ are identical to or different from each other and each represent a hydrogen atom or an alkyl group of one to four atoms, and X has the meaning mentioned above.

As concrete examples of the compound represented by the formula (III) mentioned above, the neutral compounds obtained by neutralizing the dialkylamino group-containing (meth)acrylic esters or (meth)acrylamides cited above with an acid and the quaternary ammonium salts obtained by quaternizing them with a quaternizing agent may be cited. As concrete examples of the compound represented by the formula (IV) mentioned above, the diallyl-having quaternary ammonium salts mentioned above may be cited.

The acids which are advantageously used for producing the acid-neutralized compounds mentioned above include hydrochloric acid, sulfuric acid, nitric acid, acetic acid, formic acid, maleic acid, fumaric acid, citric acid, tartaric acid, adipic acid, sulfamic acid, toluene sulfonic acid, lactic acid, pyrrolidone-2-carboxylic acid, and succinic acid, for example. The quaternizing agents which are advantageously used for producing the quaternary ammonium salts mentioned above include an alkyl halide such as methyl chloride, ethyl chloride, methyl bromide and methyl iodide, and standard alkylating agents such as dimethyl sulfate, diethyl sulfate and di-n-propyl sulfate, for example.

Of the compounds represented by the general formula (III) or (IV) mentioned above, those which prove to be particularly advantageous include the quaternary ammonium salts obtained by quaternizing dimethylaminoethyl (meth)acrylate, diethylaminoethyl (meth)acrylate, dimethylaminopropyl (meth)acrylamide, and diethylaminopropyl (meth)acrylamide with such a quaternizing agent as mentioned above or dimethyldiallyl ammonium chloride, for example. The acid-neutralized monomers involved herein are at a disadvantage in being deficient in stability of viscosity because the neutralized acids are dissociated as by the pH status of the system to induce alteration of the polymer structure. Even from this point of view, the quaternary ammonium salt monomers prove to be preferable.

[Hydrophilic nonionic group-containing vinyl monomer]

As concrete examples of the hydrophilic nonionic group-containing vinyl monomer represented by the formula (I) mentioned above, i.e. one of the component monomers forming the cationic group-containing copolymer of the present invention, (meth)acrylamide, N-methyl (meth)acrylamide, N,N-dimethyl (meth)acryl amide, N,N-diethyl (meth)acrylamide, N-n-propyl (meth)acrylamide, N-isopropyl (meth)acrylamide, N-t-butyl (meth)acrylamide and N-isobutyl (meth)acrylamide may be cited. As a concrete example of the hydrophilic nonionic group-containing vinyl monomer represented by the formula (II) mentioned above, N-(meth)acroyl morpholine may be cited. The present invention does not need to limit the vinyl monomer under discussion to those compounds cited above. It allows these hydrophilic nonionic group-containing vinyl monomers to be used singly or in the form of a mixture of two or more members.

Among other hydrophilic nonionic group-containing vinyl monomers enumerated above, N,N-di-substituted acrylamides are used particularly advantageously in terms of tactile sensation. Further, N,N-dimethyl (meth)acrylamide and N,N-diethyl (meth)acrylamide prove to be especially advantageous in respect that they find utility in a wider range of applications because they are capable of gelling even the aqueous ethanol solution or the aqueous anionic active agent solution.

[Cross-linking vinyl monomer containing at least two vinyl groups in the molecular unit thereof]

As concrete examples of the cross-linking vinyl monomer containing at least two vinyl groups in the molecular unit thereof, i.e. one of the component monomers which form the cationic group-containing copolymer of the present invention, (meth)acrylic esters of polyhydric alcohols such as ethylene glycol di(meth)acrylate, diethylene glycol di(meth)acrylate, polyethylene glycol di(meth)acrylate, propylene glycol di(meth)acrylate, dipropylene glycol di(meth)acrylate, polypropylene glycol di(meth)acrylate, 1,2-butylene glycol di(meth)acrylate, 1,3-butylene glycol di(meth)acrylate, neopentyl glycol di(meth)acrylate, glycerin di(meth)acrylate, glycerin tri(meth)acrylate, trimethylolpropane tri(meth)acrylate and pentaerythritol tetra-(meth)acrylate; acryl amides such as N-methylallyl acrylamide, N-vinyl acrylamide, N,N'-methylene bis(meth)acrylamide and bisacrylamide acetic acid; divinyl compounds such as divinyl benzene, divinyl ether and divinyl ethylene urea; polyallyl compounds such as diallyl phthalate, diallyl maleate, diallyl amine, triallyl amine, triallyl ammonium salts, allyl etherified pentaerythritol and allyl etherified sucrose containing at least two allyl ether units in the molecular unit thereof; and (meth)acrylic esters of unsaturated alcohols such as vinyl (meth)acrylate, allyl (meth)acrylate and 2-hydroxy-3-acryloyl oxypropyl (meth)acrylate may be cited.

Among other cross-linking vinyl monomers enumerated above, ethylene glycol di(meth)acrylate, polyethylene glycol di(meth)acrylate, divinyl benzene, pentaerythritol triallyl ether and pentaerythritol tetraallyl ether prove to be particularly advantageous.

[Compounding ratio of component monomers]

The mixing ratio of the cationic group-containing vinyl monomer and the hydrophilic nonionic group-containing vinyl monomer which is advantageous for the production of the cationic group-containing copolymer of the present invention is in the range of 98/2–2/98, preferably 60/40–3/97, in terms of cationic group-containing vinyl monomer/hydrophilic nonionic group-containing vinyl monomer (molar ratio). If the mixing ratio of these monomers deviates from the range mentioned above, for example, as when the proportion of the cationic group-containing vinyl monomer in the mixture exceeds the upper limit of the range mentioned above, the produced copolymer will tend to lack the thixotropy aimed at. If the proportion of the hydrophilic nonionic group-containing vinyl monomer in the mixture exceeds the upper limit of the range mentioned above, the produced copolymer will tend to suffer an undue decline in the viscosity at a low shear rate.

The proportion of the cross-linking vinyl monomer containing at least two vinyl groups in the molecular unit thereof, i.e. one of the component monomers which form the cationic group-containing copolymer of the present invention, in the total amount of the component monomers is preferably in the range of 0.002–5 wt. %, and more preferably not less than 0.002 wt. % and less than 0.1 wt. %. When the proportion of the cross-linking vinyl monomer containing at least two vinyl groups in the molecular unit thereof is less than 0.002 wt. %, the produced cationic group-containing copolymer suffers the cross-linking degree thereof to be decreased to an unduly low level and consequently the hydrogel to be formed of the cationic group-containing copolymer is not allowed to acquire high viscosity. When the proportion exceeds 5 wt. %, the hydrogel eventually produced, when placed in a hand and touched with fingers, tends to be rigid in tactile sensation and offer a poor slippage.

[Other component monomers]

The cationic group-containing copolymer of the present invention is a copolymer which has the aforementioned three vinyl monomers as essential monomer components. It may nevertheless include such other vinyl monomers as are capable of copolymerizing with these essential vinyl monomers.

As concrete examples of the other vinyl monomer answering the description, (meth)acrylic acid derivatives such as methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, n-pentyl (meth)acrylate, neopentyl (meth)acrylate, cyclopentyl (meth)acrylate, n-hexyl (meth)acrylate, cyclohexyl (meth)acrylate, n-octyl (meth)acrylate, isooctyl (meth)acrylate, 2-ethylhexyl (meth)acrylate, n-decyl (meth)acrylate, isodecyl (meth)acrylate, lauryl (meth)acrylate, tridecyl (meth)acrylate, stearyl (meth)acrylate, isostearyl (meth)acrylate, behenyl (meth)acrylate, phenyl (meth) acrylate, tolyl (meth)acrylate, xylyl (meth)acrylate, benzyl (meth)acrylate, 2-ethoxyethyl (meth)acrylate, 2-butoxyethyl (meth)acrylate, 2-phenoxy (meth)acrylate, 2-methoxypropyl (meth)acrylate, 3-methoxypropyl (meth)acrylate, 2-ethoxypropyl (meth)acrylate and 3-ethoxypropyl (meth) acrylate; anionic group-containing monomers such as 2-acrylamido-2-methylpropanesulfonic acid, sodium styrene sulfonate, acrylic acid, methacrylic acid and 2-sulfoethyl methacrylate; and betaines such as N-(3-sulfopropyl)-N-acryloyloxyethyl- N,N- dimethyl ammonium betaine, N-(3-sulfopropyl)-N-methacryloylamido propyl-N,N-dimethyl ammonium betaine, N-(3-carboxymethyl)-N-methacryloylamido propyl-N,N-dimethyl ammonium betaine, N-(3-sulfopropyl)-N-methacryloyloxy ethyl-N,N-dimethyl ammonium betaine and N-carboxymethyl-N-methacryloyloxyethyl-N,N-dimethyl ammonium betaine may be cited.

[Method of polymerization]

The method for producing the cationic group-containing copolymer of the present invention is not necessarily limited. The production, however, is generally preferred to be carried out by such methods as aqueous solution polymerization method, reversed-phase suspension polymerization method and precipitation polymerization method. As the aqueous solution polymerization method, for example, a method which comprises uniformly dissolving the monomer components and cross-linking agent in water or a hydrophilic organic solvent uniformly mixable with water or a mixed solvent thereof, removing dissolved oxygen from the interior of the reaction system as by displacement with such an inert gas as nitrogen or carbon dioxide gas, and thereafter adding a polymerization initiator to the system thereby inducing the reaction of the monomer components. The temperature of polymerization initiation is generally in the approximate range of 20–90° C. and the reaction time is in the approximate range of one to ten hours. When the monomer components to be used herein happen to be difficultly soluble in water, it is preferred to use a hydrophilic organic solvent additionally.

As typical examples of the hydrophilic organic solvent mentioned above, such lower alcohols as methyl alcohol, ethyl alcohol and propyl alcohol, such cyclic ethers as tetrahydro furan and dioxane, and acetone, acetonirtile, dimethyl formamide, dimethyl acetamide and dimethyl sulfoxide may be cited. Among other hydrophilic organic solvents mentioned above, tetrahydro-furan, acetonitrile, dimethyl formamide, dimethyl acetamide and dimethyl suloixide prove to be particularly advantageous.

As the polymerization initiator, peroxides, organic or inorganic peracids or salts thereof, or azobis-having compounds, which are capable of being uniformly dissolving in a solvent can be used. A redox reagent of a reducing agent combined with the foregoing may be used. As concrete examples of the polymerization initiator answering the description, t-butyl peroxide, t-amyl peroxide, cumyl peroxide, acetyl peroxide, propionyl peroxide, benzoyl peroxide, benzoyl isobutyryl peroxide, lauroyl peroxide, t-butyl hydroperoxide, cyclohexyl hydroperoxide, tetralin hydroperoxide, t-butyl peracetate, t-butyl perbenzoate, bis (2-ethylhexyl peroxy dicarbonate), 2,2'-azobis isobutyronitrile, phenyl azotriphenyl methane, 2,2'-azobis (2-amidinopropane) dihydrochloride, 2,2'-azobis[2-(5-methyl-2-imidazolin-2-yl)propane]dihydrochloride, 2,2'-azobis[2-(2-imidazolin-2-yl)propane]dihydrochloride, sodium persulfate, potassium persulfate, ammonium persulfate, hydrogen peroxide and the combinations of persulfates with such tertiary amines as triethyl amine, triethanol amine and dimethyl aniline may be cited.

Among other polymerization initiators mentioned above, t-butyl peroxide, benzoyl peroxide, 2,2'-azobisisobutyronitrile, 2,2'-azobis(2-amidinopropane) dihydrochloride, 2,2'-azobis[2-(5-methyl-2-imidazolin-2-yl) propane]dihydrochloride, 2,2'-azobis[2-(2-imidazolin-2-yl) propane]dihydrochloride, sodium persulfate, potassium persulfate and ammonium persulfate which are used singly or in combination with such tertiary amines as triethyl amine, triethanol amine or dimethyl aniline prove to be particularly advantageous.

The polymerizing apparatus to be used in the production of the copolymer of the present invention does not need to be particularly limited. For the aqueous solution polymerization method, for example, a container which is provided with a plurality of rotary stirring arms may be cited as the polymerizing apparatus.

The container provided with the plurality of rotary stirring arms, during the aqueous solution polymerization of the monomer mixture, must be capable of imparting shearing force originating in the rotation of the rotary stirring arms to the polymer of the form of hydrogel which is formed in consequence of the advance of the polymerization. The quantity of the rotary stirring arms provided in the container must be plural. As a container which answers the description, for example, such an apparatus as the twin arm type kneader (hereinafter referred to simply as "kneader") may be cited. During the use of the kneader, the two rotary stirring arms are rotated in mutually opposite directions at an equal speed or different speeds. When an equal speed is elected, the two rotary stirring arms are used in such a state that their radiuses of rotation may produce an overlapping part. When different speeds are elected, the two rotary stirring arms are used in such a state that their radiuses of rotation may avoid producing an overlapping part. The rotary stirring arms which are effectively used herein are known in various types such as, for example, sigma type, S type, Bambury type and fishtail type.

As one example of the procedure for producing the copolymer of the present invention, a method which comprises placing an aqueous solution containing the monomer mixture in a concentration in the range of 10–50 wt. % in a kneader fitted with a lid, optionally displacing the entrapped air in the system with such an inert gas as nitrogen, adding to the system a water-soluble radical polymerization initiator, causing the monomer mixture to initiate polymerization at normal room temperature or at an elevated temperature in the range of 30–70° C., and finely dividing with the shearing force originating in the rotation of the vanes of the kneader the polymer produced in the form of hydrogel in consequence of the advance of polymerization until completion of the polymerization may be cited. Naturally, this example is not meant to impose a limit on the scope of the present invention.

The aqueous solution of the monomer mixture to be used in this method is preferred to contain the monomer mixture in an initial concentration in the range of 10–50 wt. %.

The amount of the polymerization initiator to be used is in the range of 0.01–5 mol %, preferably 0.01–3 mol % and particularly preferably 0.01–1 mol %, based on the total amount of the monomers. Incidentally, when the amount of the polymerization initiator to be used is more than 5 mol % based on the total amount of the monomers, the produced polymer is incapable of manifesting the quality aimed at because the degree of polymerization of high polymer chains in main chains may be not increased, the proportion of high polymer chains which escape cross-linkage is increased, and the polymer becomes easily soluble in water or an organic solvent. Conversely, when this amount is smaller than 0.01 mol %, the polymerization is at a disadvantage in failing to increase the conversion of the polymerization reaction and suffering the amount of unaltered monomers to increase.

The reaction product is in the form of gel containing the solvent used in the reaction. Normally, it is pulverized as with a rotary cutter, further deprived of the solvent by the operation of heating or decompression, dried, pulverized, and classified to afford a powder.

The reversed-phase suspension polymerization method comprises uniformly dissolving the monomers and cross-linking agent in water, suspending or emulsifying the resultant aqueous solution as with the aid of a dispersing agent in an organic solvent incapable of being uniformly mixed with water, and causing the resultant suspension or emulsion to undergo a polymerization reaction. The organic solvents which are used effectively herein include, besides those already cited above, hydrocarbon such as hexane, cyclohexane, heptane, octane, benzene, toluene, xylene and ethyl benzene; halogenated hydrocarbon such as carbon tetrachloride and dichloroethane; and mineral oils such as isober, for example.

As concrete examples of the dispersing agent, sorbitan monostearate, sorbitan monopalmitate, polyvinyl alcohol, methyl cellulose, ethyl cellulose, hydroxymethyl cellulose, hydroxyethyl cellulose, carboxymethyl cellulose, carboxyethyl cellulose and sugar ester (proprietary product of Mitsubishi Kasei K.K.) may be cited.

The removal of the dissolved oxygen from the system and the treatment of the reaction product are carried out in the same manner as described above. Though the reaction conditions are not necessarily limited, they are generally as follows: The amount of the solvent to be used: 1 to 20 times, preferably 1 to 10 times, the amount of the aqueous solution of monomers, the amount of the polymerization initiator to be used: 0.01–5 mol %, preferably 0.01–3 mol %, based on the total amount of the monomers, the polymerization initiating temperature: in the approximate range of 10–90° C. and the reaction time: in the approximate range of 1–10 hours.

[Method for determination of viscosity and dynamic viscoelasticity]

The cationic group-containing copolymer of the present invention exhibits satisfactory thixotropy such that the viscosity at 25° C. of the solution prepared by incorporating the copolymer in deionized water at a concentration of 0.5 wt. % is in the range of 0.3–20 Pa·sec. at a shear rate of 1 $sec^{-1}$ and in the range of 0.01–5 Pa·sec. at a shear rate of 10 $sec^{-1}$ and the viscosity at a shear rate of 1 $sec^{-1}$ is higher than the viscosity at a shear rate of 10 $sec^{-1}$. In the present invention, the viscosity is determined by the following method.

A given cationic group-containing copolymer having an average particle diameter of not more than 50 μm was added to deionized water in such an amount as to be contained therein at an untimate concentration of 0.5 wt. % and the resultant aqueous solution was left standing at 50° C. for half a day to obtain a hydrogel. This hydrogel was tested for viscosity with a viscosimeter made by HAAKE Corp. and sold under the trademark of "Rotovisco RV-20", fitted with a measuring head R10 and a coaxial two-wall cylindrical type rotor of Sensor System SV-DIN. With a portion, 10–15 ml in volume, of the hydrogel preserved at 25° C. placed in the rotor, the viscosimeter was set measuring the viscosity of the sample at 25° C. The time program of the shear rate ($sec^{-1}$) was so set as to increase the shear rate from 0 $sec^{-1}$ to 15 $sec^{-1}$ in two minutes. The data obtained at 60 points in this while was memorized with the aid of a software, using a program of Rotation Version 2.3. The magnitudes of viscosity, η (Pa·sec.), at shear rates 1 $sec^{-1}$ and 10 $sec^{-1}$ were computed.

When the cationic group-containing copolymer of the present invention was placed in ethanol and tested for viscosity, the test was conducted by following the procedure used in the test in the deionized water while using the copolymer in a concentration of 2.0 wt. % instead.

The cationic group-containing copolymer of the present invention was tested for dynamic viscoelasticity by the following method.

A given cationic group-containing copolymer having an average particle diameter of not more than 50 μm was added to deionized water in such an amount as to be contained therein at an ultimate concentration of 0.5 wt. % to obtain a hydrogel. This hydrogel was tested at 25° C. for dynamic viscoelasticity with a dynamic viscoelasticity measuring device (made by Rheometrics Corp. and sold under the trademark designation of "Fluids Spectrometer RFS-II") in Dynamic Strain Sweep mode by the use of a cone plate having a diameter of 50 mm, a gap of 0.05 mm and a cone angle of 0.04 rad, with the frequency of strain set at 6.28 rads/sec. and the variation of strain set at 0.5–500 %.

EXAMPLES

Figure 1:
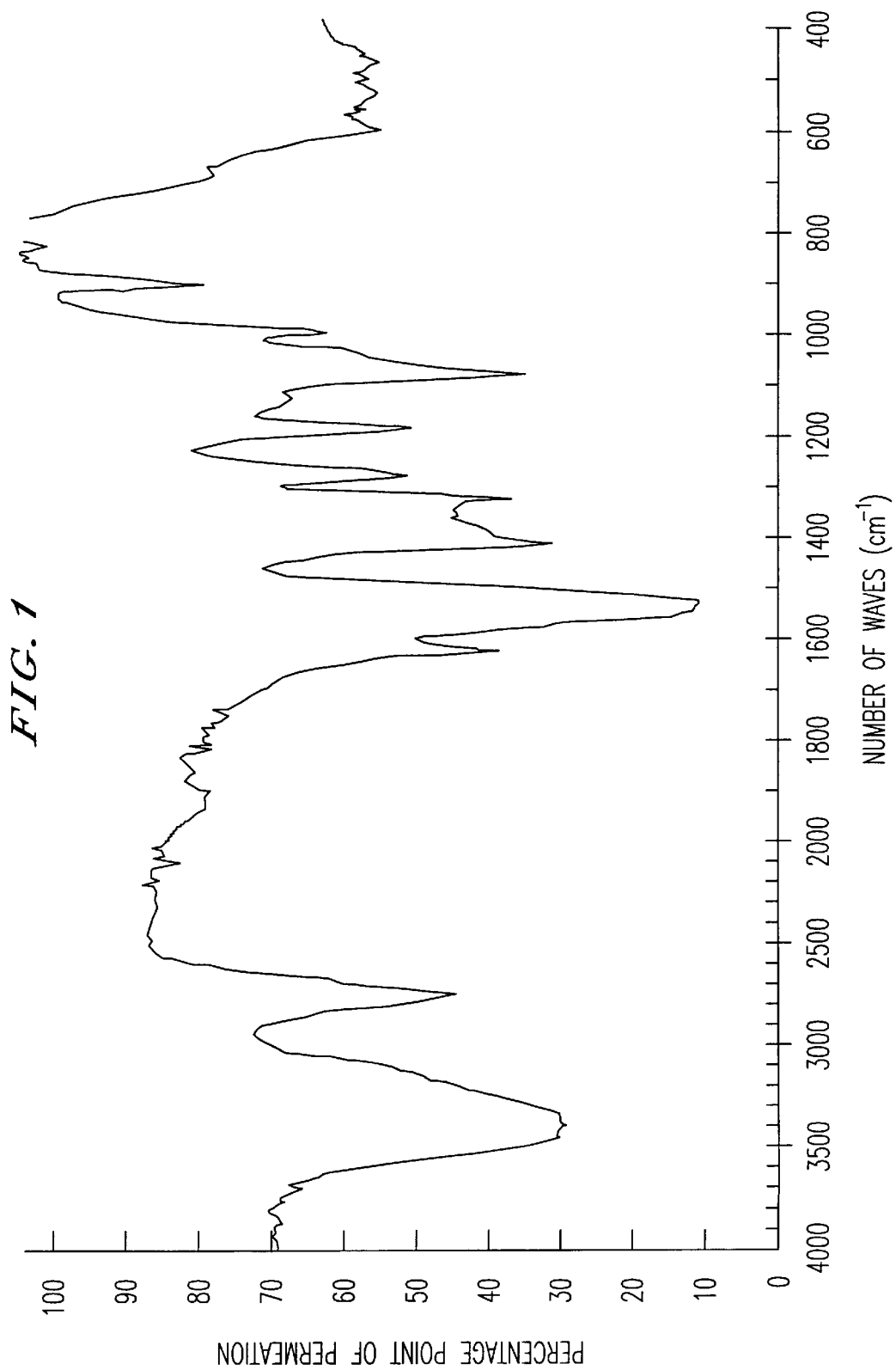
FIG. 1 is an infrared absorption spectrum of the cationic group-containing copolymer produced in Example 2.

Now, the present invention will be described more specifically below with reference to working examples and comparative examples. It should be noted, however, that the present invention is not limited to these examples.

Example 1

In a kneader of stainless steel, 1 liter in inner volume, clad in a jacket having oil of a temperature of 55° C. externally circulated therethrough and furnished with two sigma stirring arms, an aqueous monomer solution composed of 17.58 g of methyl chloride adduct of dimethylaminopropyl methacrylamide (made by Nitto Kagaku Kogyo K.K. and sold under the trademark designation of "MAPTAC"), 71.37 g of N,N-dimethyl acrylamide, 0.0429 g of polyethylene glycol dimethacrylate (made by Shin-Nakamura Kagaku K.K. and sold under the product code of "NK-9G"), and 350 g of deionized water and displaced in advance with nitrogen was placed, further swept with nitrogen gas for 20–40 minutes to displace the entrapped air in the reaction system, and heated meanwhile to elevate the temperature of the aqueous monomer solution. Then, 0.22 g of 2,2'-azobis(2-amidinopropane) dihydrochloride was added as a polymerization initiator to the aqueous monomer solution under treatment in the kneader. Within 30 minutes to one hour of adding the polymerization initiator, the aqueous monomer solution started polymerizing and formed a soft gel. The stirring was continued in the gel. Four hours after the addition of the polymerization initiator, the lid was removed from the kneader to stop the polymerization. The content of the kneader, now semi-hard in constitution, was removed from the kneader, placed in 5 liters of ethenol and washed therein by agitation for five to ten minutes, and dried. The dried product was then pulverized with a coffee mill and a jet mill. The cross-linked particles resulting from the pulverization were classified with a HiBolter Unit CPP-150 SHINTOKYO KIKAI CO, LTD to afford a cationic group-containing copolymer.

Example 2

A cationic group-containing copolymer was obtained by following the procedure of Example 1 while substituting the methyl chloride adduct of dimethylaminopropyl methacrylamide with 24.92 g of methacroyloxyethyltrimethyl ammonium chloride (made by Nitto Kagaku Kogyo K.K. and sold under the product code of "QDM"), changing the amount of the N,N-dimethyl acrylamide to 67.41 g, and substituting the polyethylene glycol dimethacrylate with 0.0103 g of pentaerythritol triallyl ether.

When this copolymer was dispersed for infrared absorption spectrum, it produced such a spectrum as is shown in FIG. 1. In the spectrum, an absorption at 1620–1650 cm$^{-1}$ (C=O stretching) due to a ternary amide structure, an absorption at 1730–1740 cm$^{-1}$ (C=O stretching) due to an ester bond and an absorption at 2900–3000 cm$^{-1}$ (CH$_2$ and CH$_3$ stretching) due to a methyl methylene bond are observed. This fact indicates that the copolymer aimed at was obtained by the procedure.

Example 3

A cationic group-containing copolymer was obtained by following the procedure of Example 1 while changing the amount of the methyl chloride adduct of dimethylaminopropyl methacryl amide to 123.1 g, the amount of the N,N-dimethyl acrylamide to 23.8 g and the amount of the polyethylene glycol dimethacrylate to 0.107 g.

Example 4

A cationic group-containing copolymer was obtained by following the procedure of Example 1 while changing the amount of the methyl chloride adduct of dimethylaminopropyl methacryl amide to 17.58 g, substituting the N,N-dimethyl acrylamide with a mixture of 67.8 g of N,N-dimethyl acrylamide and 4.58 g of N-t-butyl acrylamide and substituting the polyethylene glycol dimethacrylate with 0.0429 g of ethylene glycol dimethacrylate (made by Shin-Nakamura Kagaku K.K. and sold under the product code of "NK-1G").

Example 5

A cationic group-containing copolymer was obtained by following the procedure of Example 1 while substituting the methyl chloride adduct of dimethylaminopropyl methacrylamide with 29.85 g of an aqueous 65% diallyldimethyl ammonium chloride (made by Daiso K.K. and sold under the trademark of "DADMAC") solution and the N,N-dimethyl acrylamide with 57.8 g of N-methyl acrylamide and changing the amount of the polyethylene glycol dimethacrylate to 0.0214 g.

Example 6

A cationic group-containing copolymer was obtained by following the procedure of Example 1 while substituting the methyl chloride adduct of dimethylaminopropyl methacrylamide with 93.42 g of an aqueous 80% dimethylaminoethyl methacrylic acid diethyl sulfate (made by Nitto Kagaku Kogyo K.K. and sold under the trademark designation of "MOEDES") solution and the N,N-dimethyl acrylamide with 79.07 g of N-acroyl morpholine (made by Kojin K.K. and sold under the trademark designation of "ACMO") and changing the amount of the polyethylene glycol dimethacrylate to 0.129 g.

Comparative Example 1

A cationic group-containing copolymer was obtained by following the procedure of Example 1 while changing the amount of the methyl chloride adduct of dimethylaminopropyl methacryl amide to 8.79 g and the amount of the N,N-dimethyl acrylamide to 75.34 g and omitting the addition of the polyethylene glycol dimethacrylate.

Comparative Example 2

A cationic group-containing copolymer was obtained by following the procedure of Example 1 while omitting the addition of the methyl chloride adduct of dimethylaminopropyl methacryl amide, changing the amount of the N,N-dimethyl acrylamide to 75.34 g and substituting the polyethylene glycol dimethacrylate with 1.072 g of ethylene glycol dimethacrylate (made by Shin-Nakamura Kagaku K.K. and sold under the product code of "NK-1G").

Comparative Example 3

A cationic group-containing copolymer was obtained by following the procedure of Example 1 while changing the amount of the methyl chloride adduct of dimethylaminopropyl methacryl amide to 43.96 g, substituting the N,N-dimethyl acrylamide with 93.6 g of methoxypolyethylene glycol methacrylate (made by Shin-Nakamura Kagaku K.K. and sold under the product code of "M-90G"), and changing the amount of the polyethylene glycol dimethacrylate to 0.0214 g.

Comparative Example 4

An anionic group-containing polymer (cross-linked polymer of polyacrylic acid: made by B. F. Goodrich Co. and sold under the trademark designation of "CARBOPOL 941") was used in its unmodified form as a comparative sample.

Test Example 1

The samples prepared by adding the copolymers of Examples 1–6 and Comparative Examples 1–4 to deionized water in such an amount as to be contained therein at an ultimate concentration of 0.5 wt. % were tested for viscosity at 25° C., the samples prepared by adding the same copolymers to ethanol in such an amount as to be contained therein at an ultimate concentration of 2.0 wt. % were tested viscosity at 25° C. and the samples prepared by adding same copolymers to deionized water in such an amount to be contained therein at an ultimate concentration of 0.5% by weight were tested for dynamic viscoelasticity in aqueous solution at 25° C. The results are shown in Table 1.

TABLE 1

| | viscosity (deionized water) | | viscosity (ethanol) | | dynamic viscoelasticity | | | |
|---|---|---|---|---|---|---|---|---|
| | | | | | 1% of strain | | 500% of strain | |
| | at 1 sec$^{-1}$ (Pa·sec) | at 10 sec$^{-1}$ (Pa·sec) | at 1 sec$^{-1}$ (Pa·sec) | at 10 sec$^{-1}$ (Pa·sec) | complex modulus of elasticity (N/m$^2$) | tan δ | complex modulus of elasticity (N/m$^2$) | tan δ |
| Example | | | | | | | | |
| 1 | 2.5 | 0.5 | 6.0 | 3.0 | 2.4 | 0.98 | 1.3 | 2.28 |
| 2 | 2.0 | 0.2 | 4.0 | 2.3 | 1.4 | 1.49 | 0.5 | 3.93 |
| 3 | 5.3 | 0.7 | 4.6 | 0.9 | 31.5 | 0.37 | 3.9 | 9.61 |
| 4 | 3.0 | 0.7 | 3.1 | 1.1 | 18.2 | 0.91 | 1.5 | 2.85 |
| 5 | 13.0 | 2.5 | 11.0 | 2.3 | 132.4 | 0.20 | 7.3 | 9.12 |
| 6 | 16.5 | 3.5 | 10.6 | 3.2 | 202.0 | 0.13 | 10.8 | 12.2 |
| Comparative Example | | | | | | | | |
| 1 | 0.03 | 0.001 | 0.01 | 0.002 | 0.2 | 11.3 | 0.2 | 12.1 |
| 2 | 0.01 | 0.001 | 0.004 | 0.001 | 0.2 | 12.3 | 0.2 | 12.5 |
| 3 | 0.2 | 0.06 | 0.06 | 0.003 | 0.2 | 10.8 | 0.2 | 11.8 |
| 4 | 4.4 | 0.9 | 1.24 | 0.89 | 25.2 | 0.41 | 4.8 | 8.72 |

Test Example 2

The copolymers of Examples 1–6 and Comparative Examples 1–4 were added to deionized water in such an amount as to be contained therein at an ultimate concentration of 1.0 wt. % and the resultant aqueous solutions were left standing at 50° C. for half a day to afford viscous hydrogels. The hydrogels were tested for ease of application and intensity of residual feeling by the following methods. The results are shown in Table 2.

<Ease of Application>

The 10 members of a sensorial panel were each asked to place a 5 ml portion of a given hydrogel on the forearm of her right hand, spread it slowly with the palm of her left hand, and rate the ease of application (ease of spreading) on the following scale.

Scale of rating

1: Very easy application

2: Easy application

3: Rather easily perceivable application

4: Uneasy application

<Intensity of Residual Feeling>

The 10 members of a sensorial panel were each asked to place a 5 ml portion of a given hydrogel on the forearm of her right hand, spread it slowly with the palm of her left hand, leave it standing at rest for five minutes, rinse thoroughly the spread hydrogel with tap water, wipe the forearm with towel, and rate the tactile sensation of the skin of the forearm on the following scale.

Scale of rating

A: Strongly perceivable residual sensation

B: Perceivable residual sensation

C: Rather perceivable residual sensation

D: No perceivable residual sensation

In this case, the preferability of the hydrogel grows in proportion as the residual sensation gains in intensity.

TABLE 2

| | ease of application | intensity of residual feeling |
|---|---|---|
| Exampe 1 | 1 | A |
| Example 2 | 1 | A |
| Example 3 | 1 | A |
| Example 4 | 2 | A |
| Example 5 | 3 | A |
| Example 6 | 1 | A |
| Comparative Example 1 | 3 | C |
| Comparative Example 2 | 4 | D |
| Comparative Example 3 | 4 | B |
| Comparative Example 4 | 2 | D |

What is claimed is:

1. A cationic group-containing copolymer characterized in that a viscosity at 25° C. of the solution prepared by incorporating the copolymer in deionized water at a concentration of 0.5 wt. % is in the range of 0.3–20 Pa·sec. at a shear rate of 1 sec$^{-1}$ and in the range of 0.01–5 Pa·sec$^{31}$ 1 at a shear rate of 10 sec$^{-1}$ and the viscosity at a shear rate of 1 sec$^{-1}$ is higher than the viscosity at a shear rate of 10 sec$^{-1}$, wherein said cationic group-containing copolymer is obtained by radically polymerizing at least one cationic group-containing vinyl monomer represented by the formula (III) or (IV), at least one hydrophilic, nonionic group-containing vinyl monomer represented by the formula (I) or (II) and at least one cross-linking vinyl monomer containing at least two vinyl groups in the molecular unit thereof as an essential component monomers:

(I)

wherein $R^1$ represents a hydrogen atom or methyl group and $R^2$ and $R^3$ are identical to or different from each other and each represent a hydrogen atom or a linear or branched alkyl group or alkenyl group of one to four carbon atoms,

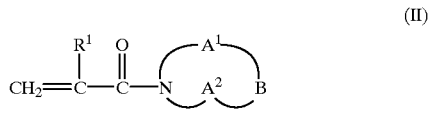
(II)

wherein $R^1$ has the meaning mentioned above, $A^1$ and $A^2$ are identical to or different from each other and each represent a group represented by the formula: —$(CH_2)_n$— in which n represents an integer of 2–6, and B represents —O— or —$CH_2$— group,

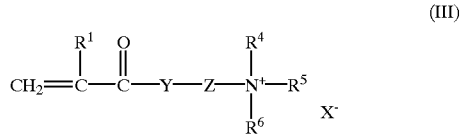
(III)

wherein $R^1$ has the meaning mentioned above, $R^4$ and $R^5$ are identical to or different from each other and each represent an alkyl group or alkenyl group of one to four carbon atoms, $R^6$ represents a hydrogen atom or an alkyl group of one to four carbon atoms, Y represents an —O—, —NH—, or —O—$CH_2CH(OH)$— group, Z represents a linear or branched alkylene group of one to four carbon atoms, and X represents a conjugate base of the acid, a halogen atom or an alkyl sulfate group of one to four carbon atoms,

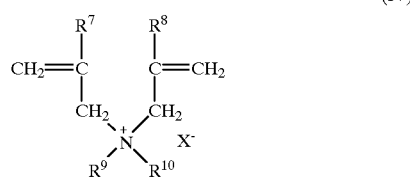
(IV)

wherein $R^7$ and $R^8$ are identical to or different from each other and each represent a hydrogen atom or methyl group, $R^9$ and $R^{10}$ are identical to or different from each other and each represent a hydrogen atom or an alkyl group of one to four carbon atoms, and X has the meaning mentioned above.

2. The cationic group-containing copolymer as claimed in claim 1, wherein an aqueous solution prepared by incorporating the copolymer in deionized water at a concentration of 0.5 wt. % exhibits at 25° C., as physical constants originating in dynamic viscoelasticity, a complex modulus of elasticity of not less than 1 N/m² and not more than 300 N/m² and a loss tangent (tan δ) of not more than 2 when the frequency is 6.28 rads/sec and the strain is 1% and a complex modulus of elasticity of not less than 0.01 N/m² and not more than 30 N/m² and a loss tangent (tan δ) of not less than 1 when the frequency is 6.28 rads/sec and the strain is 500%.

3. The cationic group-containing copolymer as claimed in claim 1, wherein an aqueous solution prepared by incorporating the copolymer in deionized water at a concentration of 0.5 wt. % exhibits at 25° C., as physical constants originating in dynamic viscoelasticity, a complex modulus of elasticity of not less than 1 N/m² and not more than 300 N/m² and a loss tangent (tan δ) of not more than 1.5 when the frequency is 6.28 rads/sec and the strain is 1% and a complex modulus of elasticity of not less than 0.01 N/m² and not more than 30 N/m² and a loss tangent (tan δ) of not less than 1 when the frequency is 6.28 rads/sec and the strain is 500%.

4. The cationic group-containing copolymer as claimed in claim 1, wherein an aqueous solution prepared by incorporating the copolymer in deionized water at a concentration of 0.5 wt. % exhibits at 25° C., as physical constants originating in dynamic viscoelasticity, a complex modulus of elasticity of not less than 1 N/m² and not more than 300 N/m² and a loss tangent (tan δ) of not more than 1 when the frequency is 6.28 rads/sec and the strain is 1% and a complex modulus of elasticity of not less than 0.01 N/m² and not more than 30 N/m² and a loss tangent (tan δ) of not less than 1 when the frequency is 6.28 rads/sec and the strain is 500%.

5. The cationic group-containing copolymer as claimed in claim 1, wherein said hydrophilic, nonionic group-containing vinyl monomer is at least one member selected from the group consisting of N,N-dimethyl (meth)acrylamide and N,N-diethyl (meth)acrylamide.

6. The cationic group-containing copolymer as claimed in claims 1, wherein an amount of the cross-linking vinyl monomer is in the range of 0.002–5 wt. % based on the total amount of the monomers.

7. The cationic group-containing copolymer as claimed in claim 1, wherein an amount of the cross-linking vinyl monomer is not less than 0.002 wt. % and less than 0.1 wt. % based on the total amount of the monomers.

8. The cationic group-containing copolymer as claimed in claim 1, wherein the viscosity at 25° C. of the solution prepared by incorporating the copolymer in ethanol at a concentration of 2.0 wt. % is in the range of 0.3–20 Pa·sec. at a shear rate of 1 sec⁻¹ and in the range of 0.01–5 Pa·sec. at a shear rate of 10 sec⁻¹ and the viscosity at a shear rate of 1 sec⁻¹ is higher than the viscosity at a shear rate of 10 sec⁻¹.

9. A thickener comprising the cationic group-containing copolymer set forth in claim 1.

* * * * *